United States Patent
Burba et al.

(10) Patent No.: US 6,436,113 B1
(45) Date of Patent: Aug. 20, 2002

(54) EYE POSITIONER

(76) Inventors: Thomas A. Burba, 2915 Everest La., Plymouth, MN (US) 55447; David R. Hardten, 710 E. 24th St., Suite 106, Minneapolis, MN (US) 55404; Neal A. Sher, 825 Nicollet Mall, Medical Arts Bldg., Minneapolis, MN (US) 55402

(*) Notice: Subject to any disclaimer, the term of this patent is extended or adjusted under 35 U.S.C. 154(b) by 0 days.

(21) Appl. No.: 09/664,464

(22) Filed: Sep. 18, 2000

(51) Int. Cl.[7] .................................................. A61F 9/00
(52) U.S. Cl. ...................................................... 606/166
(58) Field of Search .......................... 606/1, 166, 107, 606/161, 170; 600/236, 234; 604/294, 218, 235, 187, 47

(56) References Cited

U.S. PATENT DOCUMENTS

| | | | | |
|---|---|---|---|---|
| 3,074,407 A | * | 1/1963 | Moon et al. | 606/166 |
| 4,558,698 A | * | 12/1985 | O'Dell | |
| 4,619,259 A | | 10/1986 | Graybill et al. | |
| 4,688,570 A | | 8/1987 | Kramer et al. | |
| 4,718,420 A | | 1/1988 | Lemp | |
| 4,796,623 A | | 1/1989 | Krasner et al. | |
| 5,009,660 A | | 4/1991 | Clapham | |
| 5,108,412 A | | 4/1992 | Krumeich et al. | |
| 5,171,254 A | | 12/1992 | Sher | |
| 5,318,044 A | * | 6/1994 | Kilmer et al. | 128/898 |
| 5,342,378 A | * | 8/1994 | Giraud et al. | 606/166 |
| 5,433,190 A | | 7/1995 | Sunalp | |
| 5,441,040 A | | 8/1995 | Williams, Jr. | |
| 5,441,511 A | * | 8/1995 | Hanna | 606/166 |
| 5,486,188 A | * | 1/1996 | Smith | 606/166 |
| 5,556,417 A | | 9/1996 | Sher | |
| 5,569,280 A | * | 10/1996 | Kamerling | 606/166 |
| 5,601,548 A | | 2/1997 | Smith et al. | |
| 5,772,675 A | * | 6/1998 | Hellenkamp | 606/166 |
| 5,807,380 A | * | 9/1998 | Dishler | 606/166 |
| 5,861,955 A | * | 1/1999 | Gordon | 356/511 |
| 5,964,776 A | * | 10/1999 | Peyman | 606/166 |
| 5,976,163 A | | 11/1999 | Nigam | |
| 5,989,272 A | | 11/1999 | Barron et al. | |
| 5,997,559 A | * | 12/1999 | Ziemer | 606/166 |
| 6,083,155 A | | 7/2000 | Trese | |
| 6,143,011 A | * | 11/2000 | Hood et al. | 606/166 |

* cited by examiner

*Primary Examiner*—Brian L. Casler
*Assistant Examiner*—Cris L. Rodriguez
(74) *Attorney, Agent, or Firm*—Hugh D. Jaeger

(57) ABSTRACT

Self-contained eye positioner having an annular vacuum ring which is attached by a rigid hollow tube to a syringe. The syringe, which also functions as a handle, provides a vacuum source, the vacuum of which is communicated to the annular vacuum ring to suctionally adhere the annular vacuum ring to the eyeball. No external vacuum source is required.

3 Claims, 4 Drawing Sheets

EYE POSITIONER

BACKGROUND OF THE INVENTION

1. Field of the Invention

The present invention is for an ophthalmic instrument, and more particularly, pertains to an eye positioner which can be utilized for positioning, manipulating and fixating the eye during ophthalmology surgery, eye exams, refractive surgery, and laser treatment. It can be used in various types of refractive surgery such as PRK, LASIK, Holmium YAG, Thermokeratoplasty, various ophthalmic laser treatments such as YAG, femto second laser, dye laser, photocoagulation using various laser wavelengths, intracorneal ring insertion and removal, incisional keratotomy, ophthalmic exams, corneal surgery, and foreign body removal.

2. Description of the Prior Art

Eye fixation hand pieces are used by surgeons for engaging and holding an eye at a fixed reference position during eye surgery. Some of these hand pieces, such as the Thornton fixation ring, engage the eye with teeth or serrated edges. Others, such as the one shown in Krasner, U.S. Pat. No. 4,796,623, suggest a vacuum attachment to the eye, but painfully deform the eye between ridges. Vacuum attachment of an eye fixation device is also suggested in FIG. 2 of L'Esperance, U.S. Pat. No. 4,718,418, and in O'Dell, U.S. Pat. No. 4,558,698; but these are not hand pieces.

One device that has been proposed for use in fixating the eye of a patient is shown in Clapham, U.S. Pat. No. 5,009,660. The Clapham device utilizes a vacuum ring and purging gas system at the end of a handle which extends away from the vacuum ring handle at an angle. The vacuum ring can be secured to the eye around the cornea. The purging system is for dispersing evaporated tissue. A gas purging, eye fixation hand piece includes a vacuum ring evacuated by a suction line through a handle via connected to a vacuum pump, which a purging gas is delivered to an array of purging nozzles aimed into the vacuum ring from around an inner perimeter of the vacuum ring to direct purging gas jets toward the proximal side of vacuum ring attached to an eye that is held steady in a reference position for laser surgery. A preferably disposable and resilient eye-engaging ring is removable mounted on the vacuum ring to engage the eye around the cornea, and a spring-biased suction release valve is preferably mounted on hand piece handle for finger operation by the surgeon to release hand piece from the eye when surgery is completed. Mounting of gas purging nozzles on the hand piece automatically positions them properly for keeping the cornea clear of particles formed by laser ablation of eye tissue, once hand piece is properly fixed to the eye.

L'Esperance, U.S. Pat. No. 4,718,418, uses a vacuum ring which can be placed on the eye, but the vacuum ring is rigidly connected to an external piece of equipment (in this case, a laser used in treatment of the eye). This technique has inherent dangers, however, in that if the patient should panic or for whatever reason attempt to move away from the rigid device, serious trauma to the eye can result.

Eye Fixation Speculum, U.S. Pat. No. 5,171,254, describes an ophthalmic instrument for fixating a patient's eye during an ophthalmic procedure. The instrument includes a speculum securable against the patient's bony orbit, and a fixation ring attachable to the patient's eye, the ring including both a mechanism for fixating the ring with respect to the eye, and a mechanism for adjustably attaching the ring to the speculum. The instrument may include one or more bubble-type levels carried on the fixation ring for indicating the orientation of the ring and assisting the surgeon in orienting the eye of the patient before securing the ring to the speculum. Other devices are used with incisional devices attached to vacuum rings for RK (radial keratotomy) and with trephines. All having tubing and external vacuum sources.

Currently, ophthalmologists often merely use a pair of forceps or metal ring to stabilize the eye during such procedures. Obviously, this can be less than satisfactory, as it can be difficult to get a secure grip on the eyeball, squeezing the eye with the forceps can elevate intraocular pressure, and deform the shape of the cornea, inducing astigmatism. The most frequently used method is to ask the patient to keep their eye immobilized by fixating on an illuminated target. This is very difficult for most patients during excimer laser surgery, especially when the eyelids are being held open by a speculum and distracting noises are produced by the high energy laser striking the cornea. In radial keratotomy (RK), it is extremely important for the patient to hold the eye absolutely still when the multiple incisions of the cornea are made with the diamond scalpel or serious complications could occur. The other available fixation method is to use a pair of forceps (similar to tweezers) and firmly grasp the white portion of the eye. This is also an unsatisfactory method which causes pain for the patient and distorts the eye.

The Thornton ring consists of either a partial or complete circular ring with a series of teeth for gripping the eye at the sclera (white area) and a handle protruding at an angle from the ring. The instrument, due to the ring teeth, is painful for the patient because the anesthetic is only effective for the cornea and does not completely penetrate and anesthetize the sclera.

Forceps, a tweezers-type instrument, are also painful as they are used to grasp the eye at the sclera by pinching which often causes a hemorrhage. The cornea shape easily becomes distorted, inducing astigmatism, and the intraocular pressure rises unpredictably. Forceps has a number of drawbacks including subconjunctival hemorrhage and pain which can cause increased patient anxiety. Disadvantages can include torsion movements when a patient tries to move an eye with one point fixation and the resultant movement is incyclo or excyclotorsion. Depending on the degree of pressure exerted by the surgeon, the intraocular pressure can fluctuate greatly. In RK, the depth of each incision may vary depending on the intraocular pressure and surgeons will try to maintain a constant intraocular pressure by altering the forceps pressure on the eye. Corneal distortion also occurs depending on the force exerted and distance from the cornea of the forceps. It is not completely understood how altering the corneal shape intraoperatively during RK, LASIK and PRK effects the outcome. The use of various rings with multiples small teeth, such as the Thornton ring, eliminates some of the problems with one point fixation. However, all these methods have several drawbacks.

The invention also ensures that any modest change in the intraocular pressure of the eye is both controlled and predictable, unlike the prior art methods (such as grasping the eye with a forceps) which can induce erratic changes in intraocular pressure and concomitant distortion of the corneal topography.

The instrument also eliminates the problems encountered due to patient eye movement during exams, and ophthalmic surgery.

SUMMARY OF THE INVENTION

The general purpose of the present invention is to position and stabilize the eye during various ophthalmic procedures and examinations. It is necessary during refractive surgery such as PRK, LASIK, Holmium, YAG Thermokeratoplasty, ophthalmic laser treatments such as YAG, dye laser, femto second laser, various types of photocoagulation, intracorneal ring insertion and removal, incisional keratotomy, ophthalmic exams, corneal surgery, and foreign body removal that the eye be moved to different locations and held in position during the procedure.

The eye positioner is a hand held instrument which the surgeon can utilize to grasp, move and position the eye in any direction. The instrument handle comprises of a syringe which functions as the vacuum source to the rigidly attached vacuum ring. The vacuum ring can be connected to the syringe with solid tubing or rigidly attached in any other mechanical design. Alternatively, another design is to have the vacuum ring permanently connected to a rigid hollow tube with a Luer adapter and connected to the vacuum syringe. The vacuum ring is permanently attached at any desirable position or angle to the syringe and tubing during manufacturing. The important aspect of the instrument design is that the handle is a self-contained eye positioning device that incorporates the vacuum source, the syringe, as the instrument handle and rigidly connected to an annular vacuum ring. The vacuum level is controlled by the amount the plunger is extended and syringe capacity which causes the vacuum ring to adhere to the eye. The syringe plunger may be spring loaded to assist in the plunger retraction. The syringe then functions as an integral part of the instrument, the handle, in positioning the eye. As the syringe plunger is extracted, vacuum is created and the ring adheres to the eye. The surgeon can then position or move the eye by utilizing the syringe barrel as the instrument handle. As the plunger is extracted further outward from the syringe, the vacuum level increases and the eye becomes more firm. The surgeon has control by hand to begin, increase, decrease, or stop or release vacuum and intraocular pressure is determined by the surgeon's use of the syringe plunger. The instrument does not need any external power vacuum source to be operational and can be used in any location where a power source is unavailable.

The syringe can be of any volume and may have a spring on the plunger to assist in retracting the plunger and creating vacuum.

The device is a unitized instrument for positioning and fixating the eye. This instrument has an integral self-contained vacuum source supplied by a syringe and vacuum ring. The vacuum is supplied by a syringe and conduit to a vacuum ring which is then placed concentrically around the cornea (typically, seating on the episclera). Once the vacuum ring is placed on the eye and vacuum applied, the patient's eye can be moved or held in any position. The vacuum ring which includes a flexible sealing ring has a hemostatic effect on any traumatized blood vessels of the eye and is an effective dam in isolating the cornea from any fluids and debris during a variety of corneal surgery. This is particularly useful during the LASIK procedure. The hand held instrument is the only device to position an eye utilizing an integral vacuum source, a syringe, not requiring an external pump or power source for supplying vacuum and a vacuum ring applied to the eye.

This is in contrast to other devices for manipulating and holding the eye such as forceps and fixation rings which rely on mechanical force in grasping and securing the eye for fixation and positioning. These devices can distort the eye and cause trauma and hemorrhage.

According to one embodiment of the present invention, there is provided an eye positioner, including a syringe, the barrel of which is utilized as a handle, a syringe plunger shaft having a spring located along the shaft, a rigid tube extending from the syringe, and an annular vacuum ring comprised of an upper ring which is rigid and a flexible sealing ring which is attached to the upper ring.

One significant aspect and feature of the present invention is an eye positioner which is completely self-contained.

Another significant aspect and feature of the present invention includes a hand-operated syringe to provide vacuum to a vacuum ring.

Yet another significant aspect and feature of the present invention is that vacuum, at the vacuum ring, may be readily controlled by simply repositioning the plunger of the syringe.

Still another significant aspect and feature of the present invention is an eye positioner that offers total maneuverability of the eye and does not cause eye trauma.

An additional significant aspect and feature of the present invention is that the surgeon has control of vacuum level and eye movement.

A further significant aspect and feature of the present invention is that the device is easy to use, is hand held, and the eye can be positioned in any direction.

A still further significant aspect and feature of the present invention is the use of a sealing ring which has a number of advantages over rings which have small prongs or teeth, such as hemostasis from bleeding from corneal pannus which is common during LASIK and allows an almost bloodless dissection of the pterygium from the corneal surface. Corneal distortion is eliminated by use of the eye positioner.

Still another significant aspect and feature of the present invention is that the device presents cyclotorsion commonly seen when patients are placed in a supine position. Small amounts of rotation (5 to 10 degrees) can significantly reduce the effect of astigmatic correction during refractive surgery.

A significant aspect and feature of the present invention is a vacuum ring which acts as an effective dam to keep tears, blood and debris from the cornea during ophthalmic treatment.

A significant aspect and feature of the present invention is the use of a flexible sealing ring having arrays of eye contact rings.

Having thus described embodiments and significant aspects and features of the present invention, it is the principal object of the present invention to provide an eye positioner.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
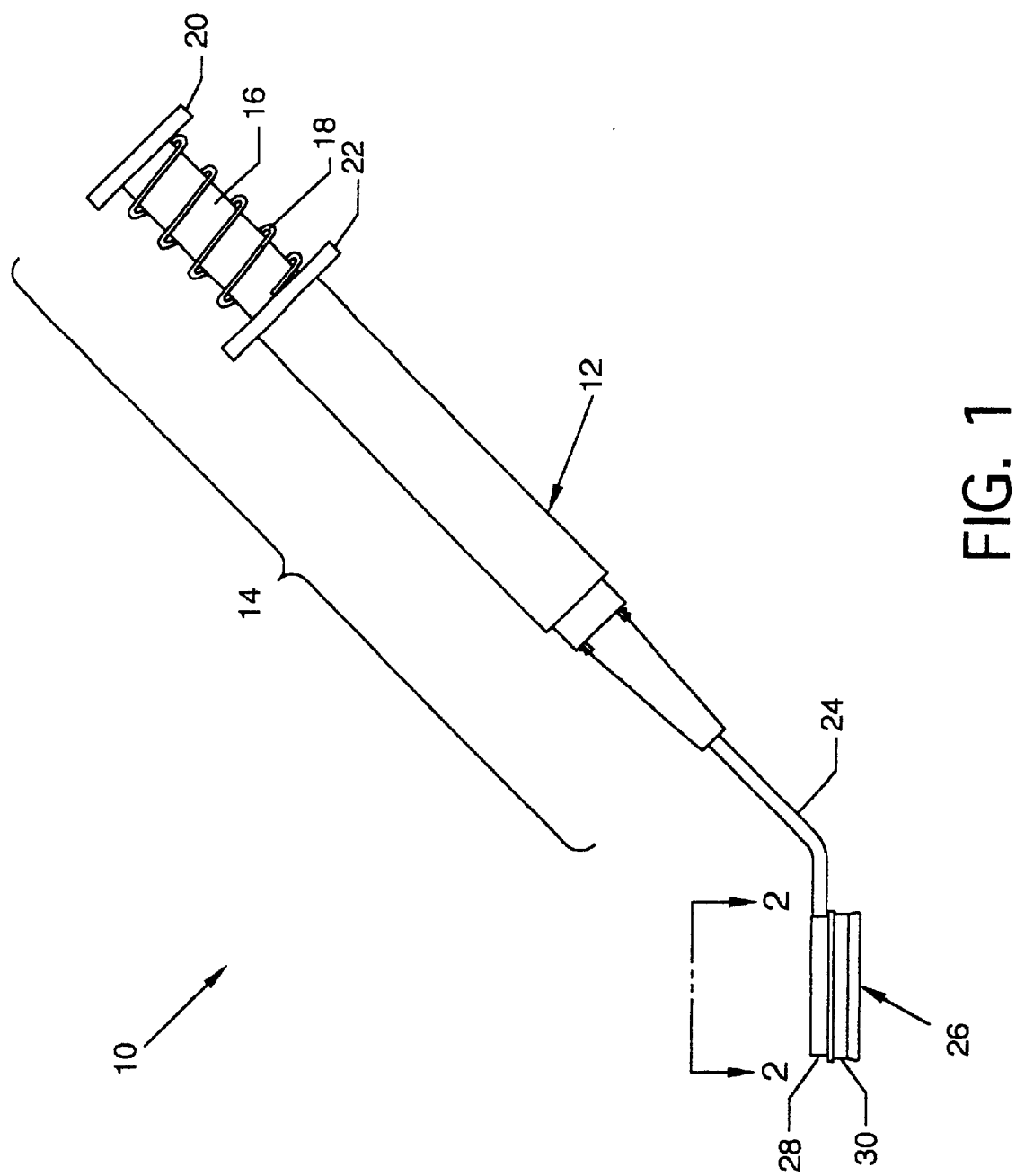
FIG. 1 illustrates a side view of an eye positioner, the present invention.

FIG. 1 illustrates a side view of an eye positioner 10, the present invention. Visible members of the eye positioner 10 includes an instrument handle 12 being the barrel of a syringe 14, a syringe plunger shaft 16, a spring 18 located over and about the syringe plunger shaft 16 and between a syringe plunger shaft planar member 20 and an annular or other shaped grasping tab 22 at one end of the syringe 14, a rigid hollow tube 24 extending from one end of the syringe 14 and an annular vacuum ring 26 located at one end of the rigid hollow tube 24. The annular vacuum ring 26 includes an upper ring 28, preferably of plastic material or other suitable material, to which the rigid hollow tube 24 attaches and connects, and a flexible sealing ring 30 formed of plastic, rubber or the like, which engages and which is held by the upper ring 28.

Figure 2:
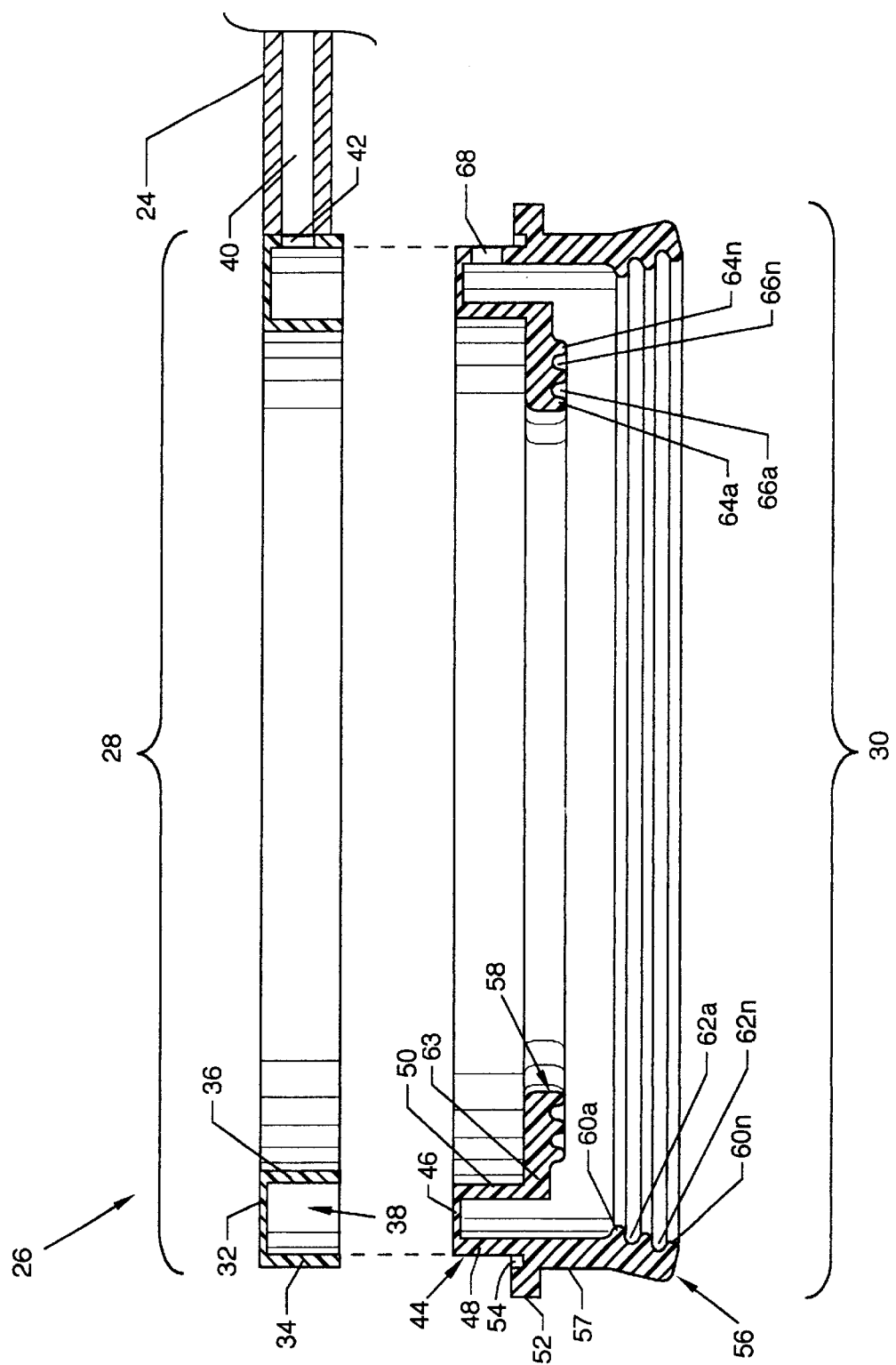
FIG. 2 illustrates an exploded cross section view of the annular vacuum ring along line 2—2 of FIG. 1.

FIG. 2 illustrates an exploded cross section view of the annular vacuum ring 26, where all numerals correspond to those elements previously described. The upper ring 28 is annular and includes a top 32 which is annular, an outer circumferential side 34 extending downwardly from the top 32, and, an inner circumferential side 36 extending downwardly from the top 32 and spaced from the outer circumferential side 34. A channel 38, being annular, is formed by the intersection of the outer circumferential side 34 and the inner circumferential side 36 with the top 32. The channel 38, being annular, accommodates a corresponding annular portion of the flexible sealing ring 30 later described in detail. The rigid hollow tube 24 attaches to the periphery of the upper ring 28. A lumen 40 central to the rigid hollow tube 24 communicates to the channel 38 through an aligned orifice 42 in the outer circumferential side 34 of the upper ring 28 and an orifice 68 in the flexible seating ring 30.

The one piece flexible sealing ring 30 includes geometrically configured members to sealingly accommodate: (1) the annular channel 38 of the upper ring 28; and (2) the human eye.

The flexible sealing ring 30 can be constructed of a suitable and flexible material such as rubber, plastic and the like, and includes a includes, in part, an upwardly extending annular connecting seal 44 the shape of which and the purpose of which is to accommodatingly and to frictionally engage and to seal with the channel 38 of the upper ring 28. The annular connecting seal 44 includes a top 46 which is annular, an outer circumferential side 48 extending downwardly from the top 46, and an inner circumferential side 50 extending downwardly from the top 46 and spaced from the outer circumferential side 48. An outwardly extending annular ring 52 intersects the lower region of the downwardly extending outer circumferential side 48 and includes a sealing groove 54 at the intersection to accommodatingly seal with the lower portion of the outer circumferential side 34 and to assist in vertical locating the upper ring 28 with respect to the flexible sealing ring 30.

Also co-located with the flexible sealing ring 30 are outer and inner flexible sealing arrays 56 and 58 which are incorporated to seal against the human eye. The outer flexible sealing array 56 is located downwardly from the junction of the outer circumferential side 48 and the annular ring 52 at the end of an intermediate sidewall portion 57 and is slightly angled from the vertical. A plurality of inwardly facing and concentric eye contact rings 60a–60n having progressively larger radii alternate with and are separated by a plurality of progressively larger radii concentric grooves 62a–62n all of which are located at the inner and lower periphery of the flexible sealing ring 30. The inner flexible sealing array 58 extends inwardly from and is oriented in horizontal fashion from the lower region of the inner circumferential side 50 via an intermediate connecting wall 63. When viewed in cross section, inner circumferential side 50 of the one-piece flexible sealing ring 30 may be described as having an L-shaped cross section with a first leg of the generally L-shaped cross section extending upwardly into ring 26 as side 50 and the second leg extending inwardly as wall 63. A plurality of downwardly facing and concentric eye contact rings 64a–64n having progressively larger radii alternate with and are separated by a plurality of progressively larger radii concentric grooves 66a–66n all of which are located central to the flexible sealing ring 30. An orifice 68 is located in the outer circumferential side 48 of the flexible seating ring 30. The orifice 68 aligns with the orifice 42 of the upper ring 28 and with the lumen 40 of the rigid hollow tube 24.

The syringe and ring can be manufactured from a variety of suitable materials, such as metal or plastic or any suitable material. Different syringe capacities can be used to change vacuum level. Ring of various diameters can be utilized. The vacuum pump in instrument handle can be any mechanical pump, such as a syringe or hand pump. The vacuum pump can also be powered by electricity, such as battery or other electric supplies. The ring can be a complete circle or have an open section for accessibility of instruments.

Figure 3:
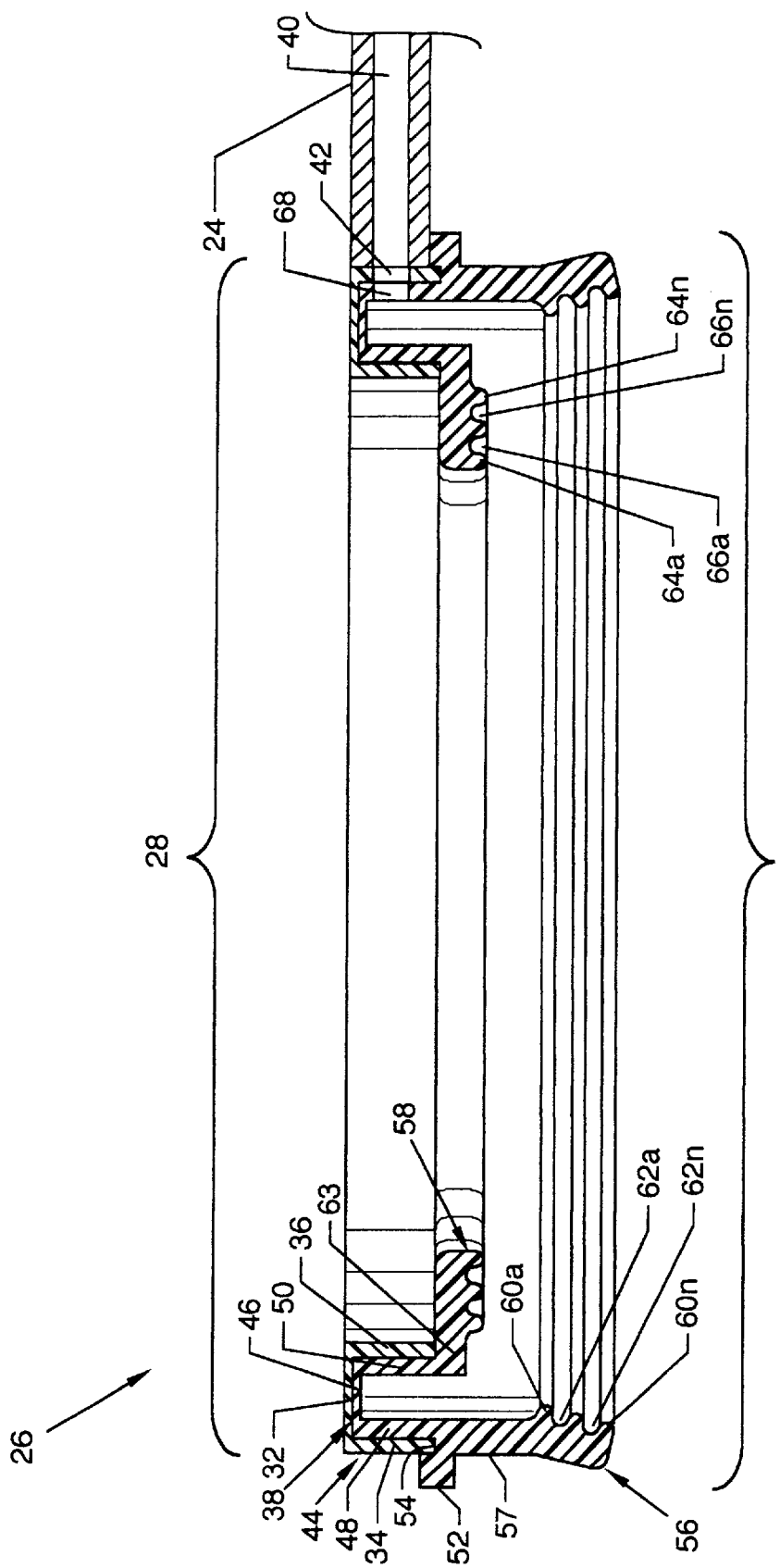
FIG. 3 illustrates an assembled cross sectional view of the annular vacuum ring illustrated in FIG. 2; and, FIG. 4 illustrates the annular vacuum ring of FIG. 3 engaging an eye.

FIG. 3 illustrates an assembled cross section view of the annular vacuum ring 26, where all numerals correspond to those elements previously described. Illustrated in particular is the mutual engagement and accommodational relationship of the annular connecting seal 44 of the flexible sealing ring 30 to the annular channel 38 of the upper ring 28. Also shown is the relationship of the lumen 40 of the rigid hollow tube 24 which communicates with the flexible sealing ring 30 through orifices 42 and 68 of the flexible sealing ring and of the upper ring 30 and 28, respectively. The upper ring 28 provides support for the flexible sealing ring 30.

MODE OF OPERATION

Figure 4:
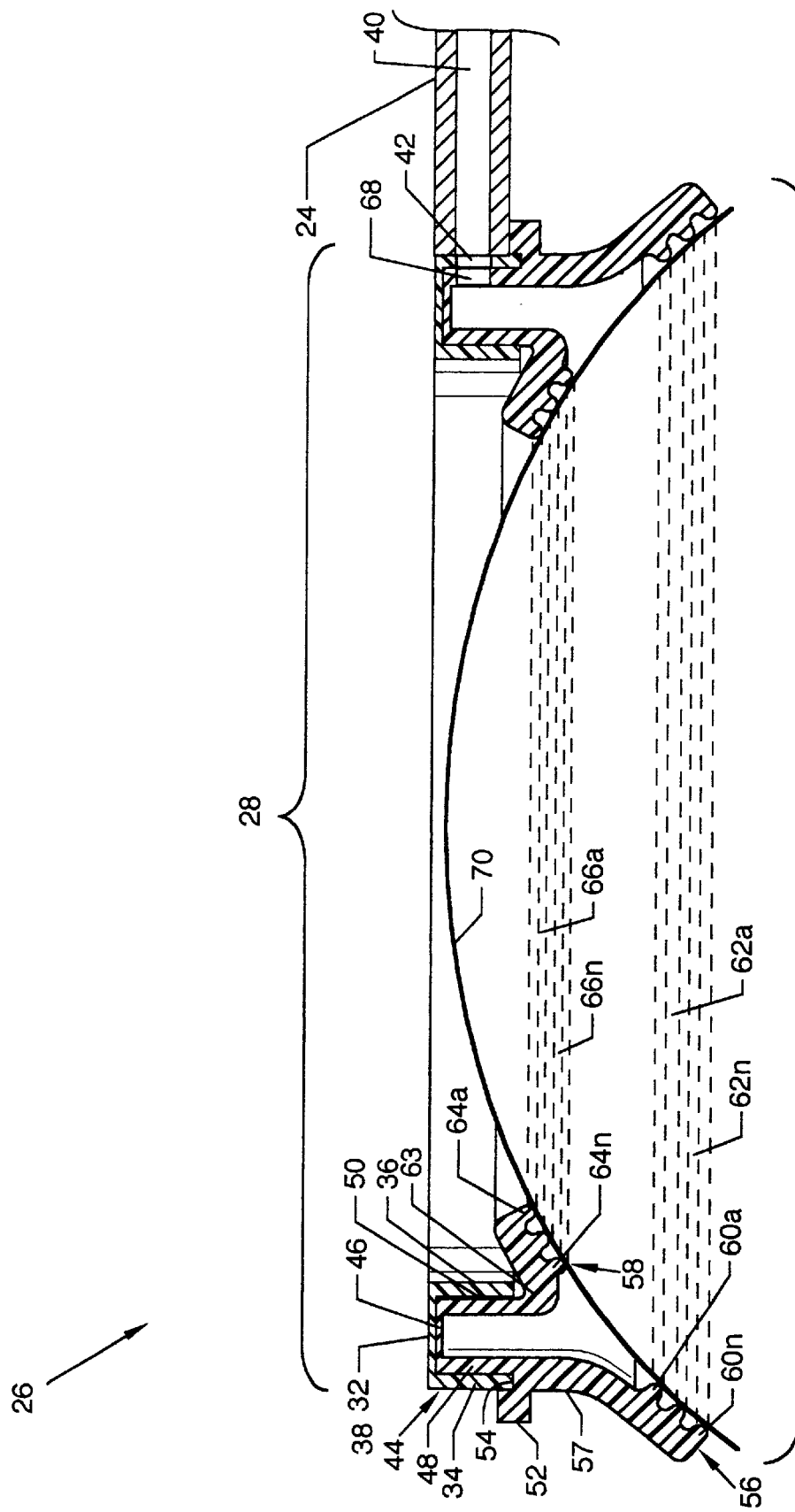

FIG. 4 illustrates the mode of operation, where all numerals correspond to those elements previously described. The annular vacuum ring 26 is aligned in gentle contact to engage the eye 70 just outside the limbus. The annular vacuum ring 26 is positioned manually to cause the outer flexible sealing array 56 and the inner flexible sealing array 58 to flex about the intermediate sidewall 57 and the intermediate connecting wall 63, respectively, whereby the outer flexible sealing array 56 and the inner flexible sealing array 58 flexibly align to the contour of the eye 70. Subsequent to suitable engagement, the syringe plunger shaft 16 is suitably actuated outwardly to cause sufficient vacuum to be created between the members of the flexible sealing ring 30 and the arcuate area of the eye 70 encompassed by the eye contact rings 60a–60n of the outer flexible sealing array 26 and the eye contact rings 64a–64n of the inner flexible sealing array 58. Such action allows the eye 70 to be grasped and suitably positioned for surgical or other techniques. Spring 18 assists the outward movement of the syringe plunger shaft 16.

Various modification can be made to the present invention without departing from the apparent scope hereof.

EYE POSITIONER

PARTS LIST 10 eye positioner
12 instrument handle 14 syringe
16 syringe plunger shaft
18 spring
20 syringe plunger shaft planar member
22 grasping tab
24 rigid hollow tube
26 annular vacuum ring
28 upper ring
30 flexible sealing ring
32 top
34 outer circumferential side
36 inner circumferential side
38 channel
40 lumen
42 orifice
44 annular connecting seal
46 top
48 outer circumferential side
50 inner circumferential side
52 annular ring
54 sealing groove
56 outer flexible sealing array
57 intermediate sidewall
58 inner flexible sealing array
60a–n eye contact rings
62a–n grooves
63 intermediate connecting wall
64a–n eye contact rings
66a–n grooves
68 orifice
70 eye

What is claimed is:

1. An eye positioner, comprising:
   a. a syringe, the syringe including:
      i. a barrel, the barrel having a first end, a second end, an interior, and an exterior, the exterior being suitable for grasping as a handle;
      ii. a grasping tab attached at the first end of the barrel of the syringe;
      iii. a syringe plunger shaft, the syringe plunger shaft being slideable within the interior of the barrel of the syringe, the syringe plunger shaft having a protruding end extending from the first end of the barrel of the syringe, with a syringe plunger shaft planar member at the protruding end of the syringe plunger shaft, the syringe plunger shaft planar member oriented to facilitate deeper insertion of the syringe plunger shaft; and,
      iv. a spring, the spring being located over and about the syringe plunger shaft and between grasping tab and the syringe plunger shaft planar member, such that the spring urges the syringe plunger shaft to a partially extended position, relative to the syringe barrel;
   b. a rigid hollow tube, the rigid hollow tube having a first end, a second end, and a lumen extending therethrough, the first end of the rigid hollow tube connected to the second end of the barrel of the syringe and the lumen in fluid communication with the interior of the syringe;
   c. an upper ring, the upper ring having a top, an inner circumferential side, and an outer circumferential side spaced apart from the inner circumferential side, the top, the inner circumferential side and the outer circumferential side together defining an annular channel between the inner circumferential side and the outer circumferential side, the outer circumferential side connected to the second end of the rigid hollow tube and having an orifice allowing fluid communication with the lumen of the rigid hollow tube;
   d. a flexible sealing ring, the flexible sealing ring including:
      i. a top, having a ring shape;
      ii. an outer circumferential side depending from the top, the outer circumferential side having an orifice aligned with the orifice of the upper ring and enabling fluid communication with the lumen of the rigid hollow tube, the outer circumferential side further having an intermediate sidewall extending downwardly therefrom;
      iii. an inner circumferential side, spaced apart from the outer circumferential side and depending from the top, wherein the top, inner circumferential side and outer circumferential side together engage and are held in the annular channel of the upper ring and are supported thereby, the inner circumferential side further having an intermediate connecting wall extending therefrom and the intermediate connecting wall having a generally L-shaped cross-section with a first leg of the generally L-shaped cross-section being connected to the inner circumferential side and a second leg directed inwardly;
      iv. an inner flexible sealing array, carried by the second leg of the generally L-shaped cross-section of the intermediate connecting wall, the inner flexible sealing array comprising a plurality of eye-contact rings, each of the rings of the plurality being separated from adjoining rings of the plurality by a groove, the array being generally directed away from the syringe; and,
      v. an outer flexible sealing array connected to the intermediate sidewall associated with the outer circumferential side of the flexible sealing ring, the outer sealing array carrying a second plurality of eye-contact rings, each of the eye-contact rings of the second plurality being separated from adjoining rings of the second plurality by a groove, the outer flexible sealing array being generally directed inwardly, and wherein the inner sealing array and the outer sealing array together tend to diverge to adapt to the surface of an eye such that production of vacuum between the inner sealing array and the outer sealing array whilst in adapted contact with an eye causes the inner and outer sealing arrays to mutually interact with the eye to stabilize the eye.

2. The eye positioner of claim 1, wherein the rigid hollow tube has a bend located intermediate the first end and the second end.

3. The eye positioner of claim 1, wherein the rigid hollow tube is radially oriented with respect to the upper ring.

* * * * *